United States Patent [19]

Rooks

[11] Patent Number: 5,719,952
[45] Date of Patent: Feb. 17, 1998

[54] INSPECTION SYSTEM FOR CROSS-SECTIONAL IMAGING

[75] Inventor: Stephen Michael Rooks, Willowdale, Canada

[73] Assignee: International Business Machines Corporation, Armonk, N.Y.

[21] Appl. No.: 645,946

[22] Filed: May 14, 1996

Related U.S. Application Data

[63] Continuation of Ser. No. 300,677, Sep. 2, 1994, Pat. No. 5,592,562.

[30] Foreign Application Priority Data

Jan. 19, 1994 [CA] Canada ................. 2113752

[51] Int. Cl.⁶ ..................................... G06K 9/00
[52] U.S. Cl. ................. 382/150; 382/149; 378/22
[58] Field of Search .................. 382/149, 150; 378/22

[56] References Cited

U.S. PATENT DOCUMENTS

| | | | |
|---|---|---|---|
| 4,766,670 | 8/1988 | Gazdik et al. | 29/830 |
| 4,809,308 | 2/1989 | Adams et al. | 378/99 |
| 4,852,131 | 7/1989 | Armistead | 378/4 |
| 4,926,452 | 5/1990 | Baker et al. | 378/22 |
| 5,081,656 | 1/1992 | Baker et al. | 378/21 |
| 5,097,492 | 3/1992 | Baker et al. | 378/22 |
| 5,164,994 | 11/1992 | Bushroe | 382/8 |
| 5,170,444 | 12/1992 | Yamanaka | 382/55 |
| 5,291,535 | 3/1994 | Baker et al. | 378/22 |
| 5,395,040 | 3/1995 | Holzmann | 228/254 |
| 5,455,870 | 10/1995 | Sepai et al. | 382/147 |
| 5,473,814 | 12/1995 | White | 29/840 |

FOREIGN PATENT DOCUMENTS

0433803A1 12/1989 European Pat. Off. ....... G01N 23/18

OTHER PUBLICATIONS

S. M Thomas, et al. "A Simple Approach for the Estimation of Circular Arc Center and Its Radius" Computer Vision, Graphics, and Image Processing 45, pp. 362–370, 1989.

E. F. Cappo, et al. "Highly Manufacturable Multi–Layered Ceramic Surface Mounted Package" IEEE/CHMT IEMT Symposium, pp. 424–428, 1991.

*Primary Examiner*—Jose L. Couso
*Assistant Examiner*—Anh Hong Do
*Attorney, Agent, or Firm*—H. Daniel Schnurmann

[57] ABSTRACT

A method and apparatus for inspecting a bonded joint between components. A cross-sectional image of the joint is analyzed by determining the location of a first characteristic of the joint, the centroid of the joint in the cross-sectional image; and then measuring a second characteristic of the joint in reference to the location of the centroid. This measurement may be used by comparing it with a predetermined specification expected for the measurement for the purpose of determining the quality of the joint. The invention is particularly advantageous for studying cross-sectional X-ray images of solder joints between electronic components and substrata upon which they are mounted and can be implemented for analyzing the images produced in cross-sectional X-ray inspection machines such as scanned beam X-ray laminography systems or digital tomosynthesis systems.

25 Claims, 18 Drawing Sheets

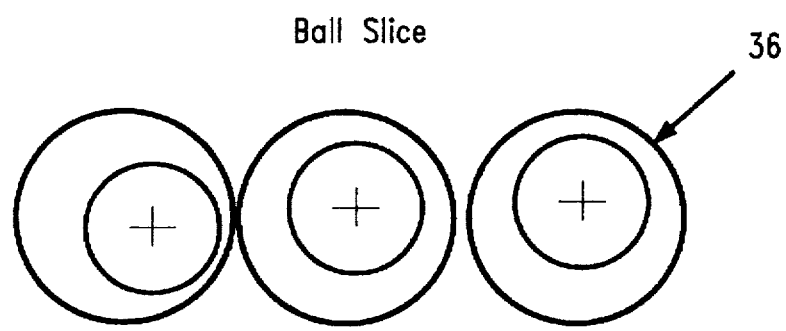
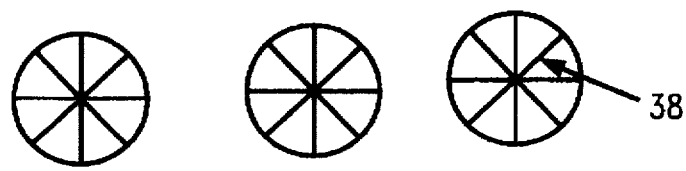
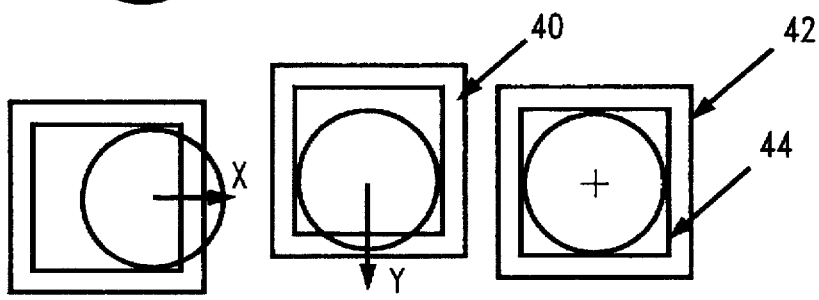
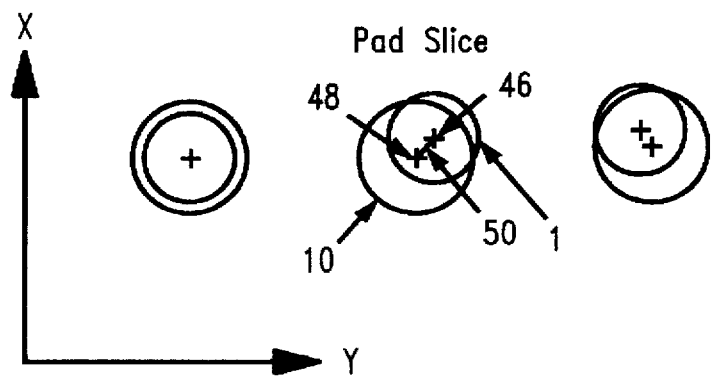
FIG. 8 a
FIG. 8 b
FIG. 8 c
FIG. 8 d

INSPECTION SYSTEM FOR CROSS-SECTIONAL IMAGING

This is a Continuation patent application of U.S. patent application Ser. No. 08/300,677, filed on Sep. 2, 1994, now U.S. Pat. No. 5,592,562.

FIELD OF THE INVENTION

This invention related generally to the inspection of interconnections between electronic devices or components using cross-sectional imaging inspection.

BACKGROUND OF THE INVENTION

Since the introduction of Integrated-Circuit (IC) chips, the conventional technique for mounting them on Printed-Circuit Boards (PCBs) has been the Pin-Through-Hole 10. (PTH) technology. However, continual increases in IC-chip complexity, performance, and placement density are placing demands on the density and functionality of package interconnections influencing the development of various Surface-Mount-Technology (SMT) package-interconnection techniques to satisfy the needs, such as the Ball-Grid-Array (BGA) interconnection technique. These techniques are documented in an article by F. F. Cappo, et al. entitled "Highly Manufacturable Multi-layered Ceramic Surface-Mounted Package," IEEE/CHMT IEMT Symposium 1991, pp. 424–428, September 1991. Ball-Grid-Array is an area-array interconnection that can achieve a density of 400 interconnections per square inch. Because of the complexity or density of interconnections, a number of techniques have been developed to monitor interconnection quality.

Various automated solder-inspection systems are commercially available for monitoring solder-joint quality. The techniques used in these systems can be characterized by the radiation employed (either infrared, visible light, X-ray, or acoustic), the way in which the radiation interacts with the object being inspected, and the means used to detect the response of the radiation. The types of radiation can be subdivided into two broad categories, namely, non-penetrating and penetrating, depending on whether the radiation can penetrate the intervening chip-package material to image the Ball-Grid-Array joints. Techniques using penetrating radiation, such as acoustic and X-ray, can potentially inspect all Ball-Grid-Array joints within an area array including both peripheral joints and joints hidden under the chip-package material. The image generated by transmission systems (as opposed to cross-sectional systems) are due to the combined attenuation of the beam by every feature along its path. Therefore, the individual contribution to the attenuation of the beam by distinct features along the same beam path cannot be singularly isolated. For example, with respect to Ball-Grid-Array joints, the supporting solder ball with its high-lead content would entirely obscure the eutectic-solder fillets in a transmission image. For these reasons transmission systems tend not to be effective for the inspection of Ball-Grid-Array joints. However, cross-sectional inspection techniques have proven to be effective, as disclosed in the following patents:

U.S. Pat. No. 5,097,492 issued Mar. 17, 1992 and U.S. Pat. No. 4,926,452, issued May 15, 1990, both to Bruce D. Baker, et al., describe an inspection system using cross-sectional imaging to inspect microelectronic devices. U.S. Pat. No. 4,809,308 issued Feb. 28, 1989 to John Adams, et al. describes a transmission X-Ray inspection system.

Although cross-sectional imaging described above is useful for inspection, a number of interconnection or soldering defects are not reliably detected by these systems.

These references fail to disclose the use of the centroid of a cross-sectional image of an interconnection as a reference (location) for the measurement of a characteristic of the interconnection to determine the quality of the interconnection. The use of the image centroid of the interconnection has been determined to dramatically improve measurement accuracy in inspection so that defects and good joints can be more reliably distinguished, especially in the Ball-Grid-Array joint environment.

While Ball-Grid-Array (BGA) is compatible with existing assembly processes, and is functionally superior to Pin Through Hole (PTH), Ball-Grid-Array cannot successfully replace PTH unless it can also provide the same long-term reliability. The solder-joint volume and ball/pad alignment are the most critical characteristics that the assembly process for Ball-Grid-Array must consistently produce to ensure long-term reliability. Furthermore, the assembly process must be controlled to minimize such process defects as pad nonwets and solder bridges. To develop and control such a robust assembly process requires the use of an inspection technique to characterize the process by quantitatively measuring the critical characteristics of Ball-Grid-Array joints, such as the solder-joint volume and the ball/pad alignment. To this end, the overriding emphasis of inspection is to provide data on the assembly process that can be used to improve it in a closed-loop manner and not simply to screen the assembly-process output for defects. However, the Ball-Grid-Array technology poses a significant challenge to developing a satisfactory inspection process because the eutectic solder fillets that require inspection are obscured by the high-lead-content solder balls and a highly-metallized ceramic substrate. Thus, in order to reliably inspect the solder fillets, the inspection system must be able to isolate the solder fillets from the solder balls and the ceramic substrate. The method invention provides a suitable inspection system for these purposes.

BRIEF DESCRIPTION OF THE DRAWINGS

FIG. 8 shows a technique for determinating the location of image centroids.

TECHNICAL DESCRIPTION OF THE PREFERRED EMBODIMENT

Figure 1:
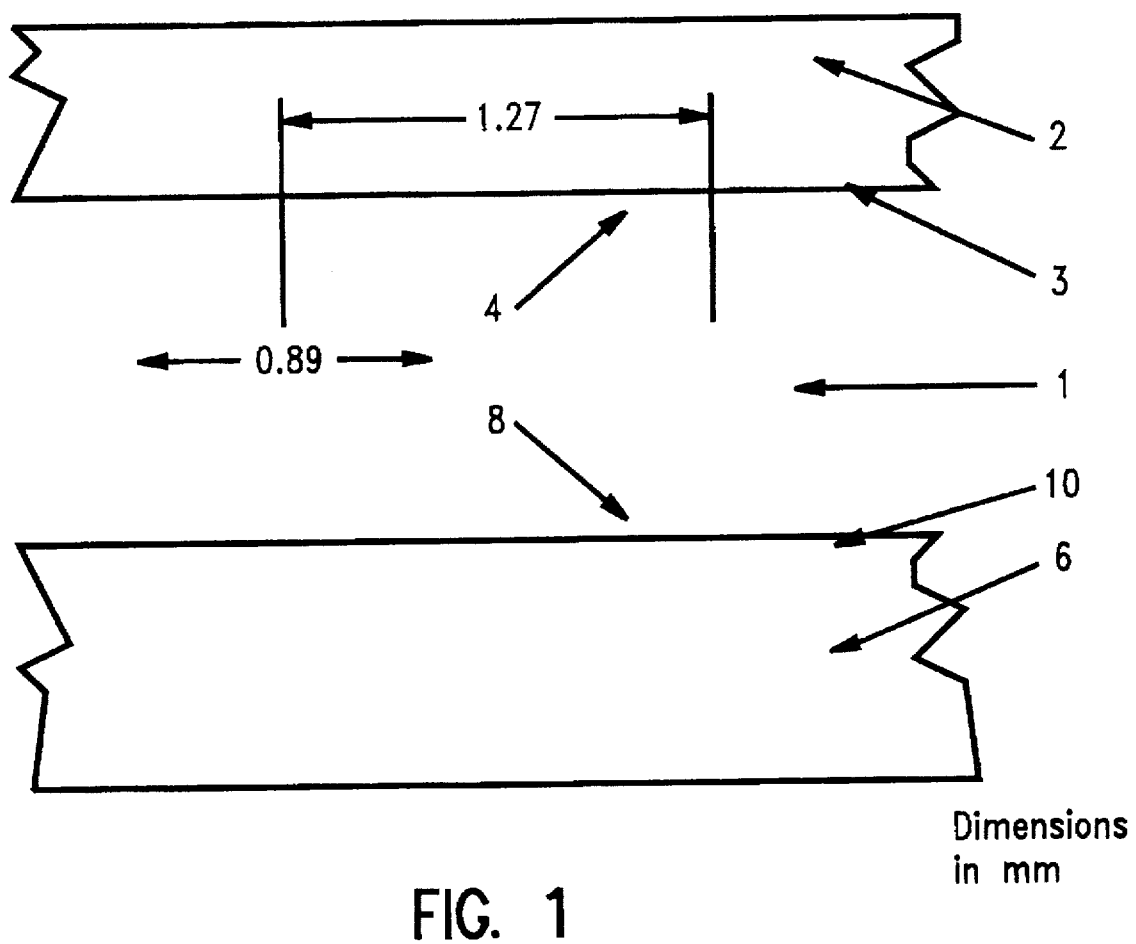
FIG. 1 shows a basic Ball-Grid-Array structure.

FIG. 1 depicts a Ball-Grid-Array structure capable of being inspected by the present invention.

The particular Ball-Grid-Array joint structure described consists of 90% Pb/10% Sn solder balls 1, 0.89 mm in diameter, that are attached to circular pads 3 on the underside of a ceramic chip package 2 at a pitch of 1.27 mm with 63% Sn/37% Pb eutectic solder 4. The resulting surface-mount package is typically attached to a printed-circuit board (PCB) 6 by placing it into 63% Sn/37% Pb eutectic solder-paste 8 screened on circular copper pads 10, and reflowing the assembly in an infrared or hot-air convection oven. During reflow, surface tension minimizes the surface free-energy of the eutectic-solder fillets by dynamically centering the balls. The solder ball provides the necessary standoff between the ceramic package and the PCB to relieve the shear strains induced by the Coefficient of Thermal Expansion mismatch experienced during power cycling.

Figure 2A:
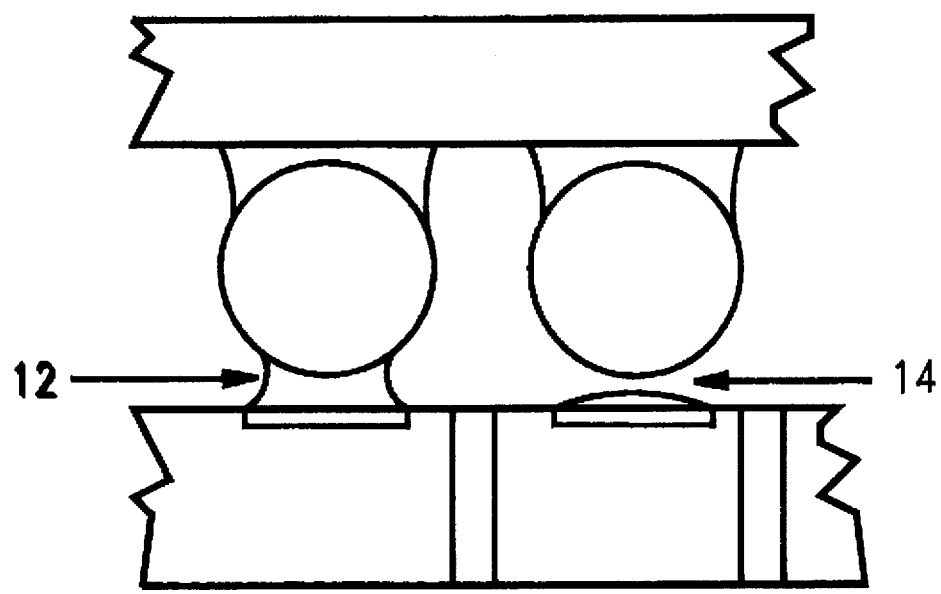
FIG. 2 shows low-solder and open conditions.
Figure 2B:
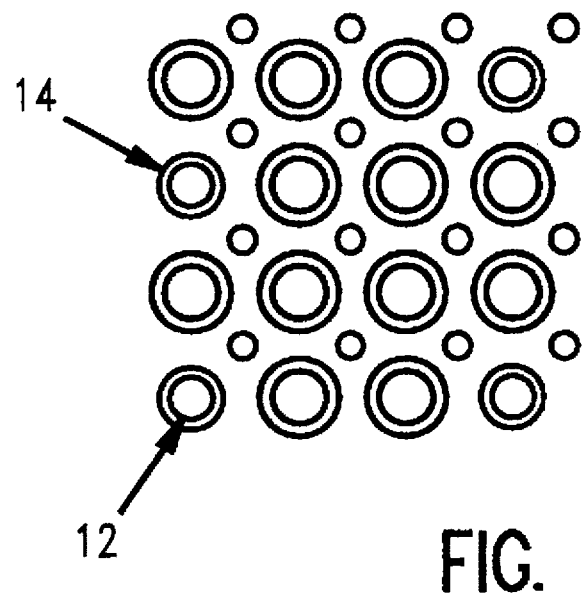

The most critical feature for maximizing the fatigue life of a Ball-Grid-Array joint is the volume of the solder fillet 8 (pad fillet) between the ball 1 and the PCB pad 10, which is characterized by the diameter at its minimum cross-section and must be sufficient to withstand the stresses experienced during power cycling. Furthermore, the centroid of the solder ball should be aligned with the centers of the package and PCB pads, to further reduce the joints susceptibility to fatigue failure. Therefore, solder volume and ball/pad alignment are the most critical interconnection characteristics which the assembly process for Ball-Grid-Array must consistently produce to ensure long-term reliability. Based on experience with the standard SMT-assembly process and on experience drawn from the recent Ball-Grid-Array assembly process development, potential Ball-Grid-Array joint defects are shown and described in the following figures:

FIG. 2 depicts low-solder and open conditions. A low-solder Ball-Grid-Array joint 12 lacks sufficient solder to properly attach the solder ball to the copper pad on the PCB, which may lead to fatigue cracking. An open condition 14 is an extreme form of low-solder joint in which the solder makes no contact between the ball and the copper pad. Both open and low-solder joints are caused by either poor screening of the solder paste or by poor wetting of the molten solder to the copper pad surface.

Figure 3:
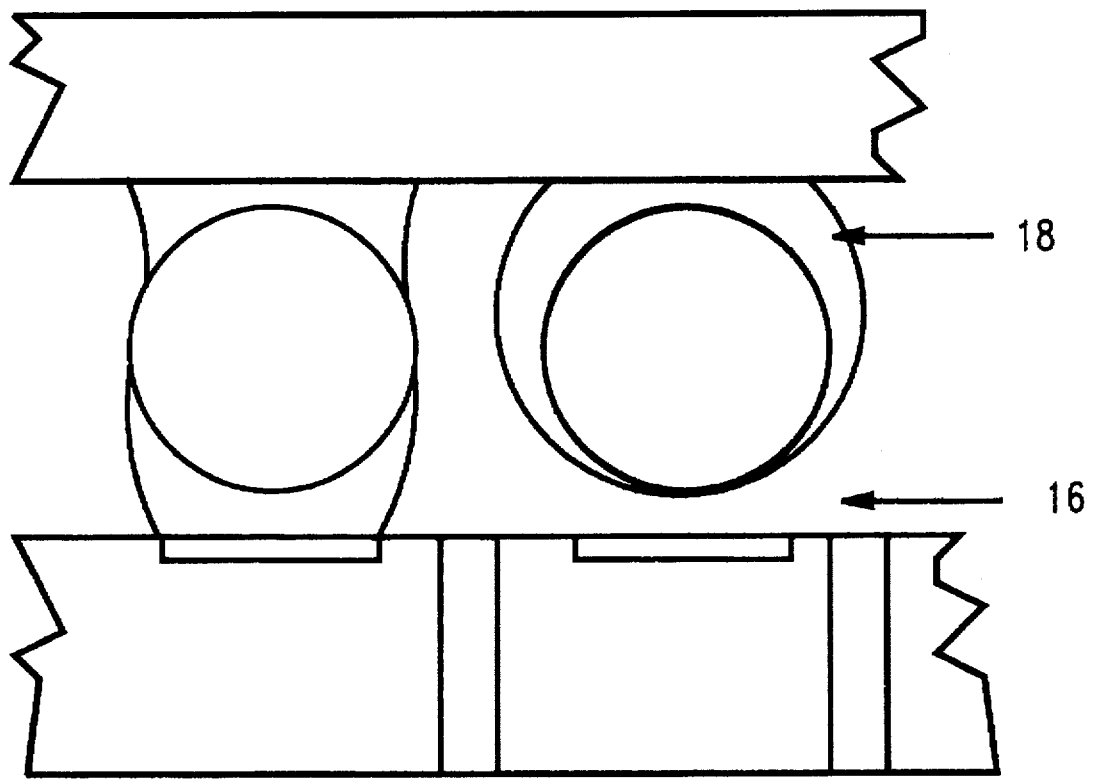
FIG. 3 illustrates a pad non-wet condition.

FIG. 3 depicts pad-nonwet condition. This condition is characterized by an open 16 or a low-solder condition between the solder ball and the PCB pad, and an increased volume of solder 18 between the ball and the pad of the chip package. Poor wetting of the molten solder to the copper pad due to contamination or poor flux activity causes a pad nonwet. Since the molten solder cannot wet the PCB pad but readily wets the solder ball, capillary attraction draws the molten solder up the ball to the chip-package level.

Figure 4A:
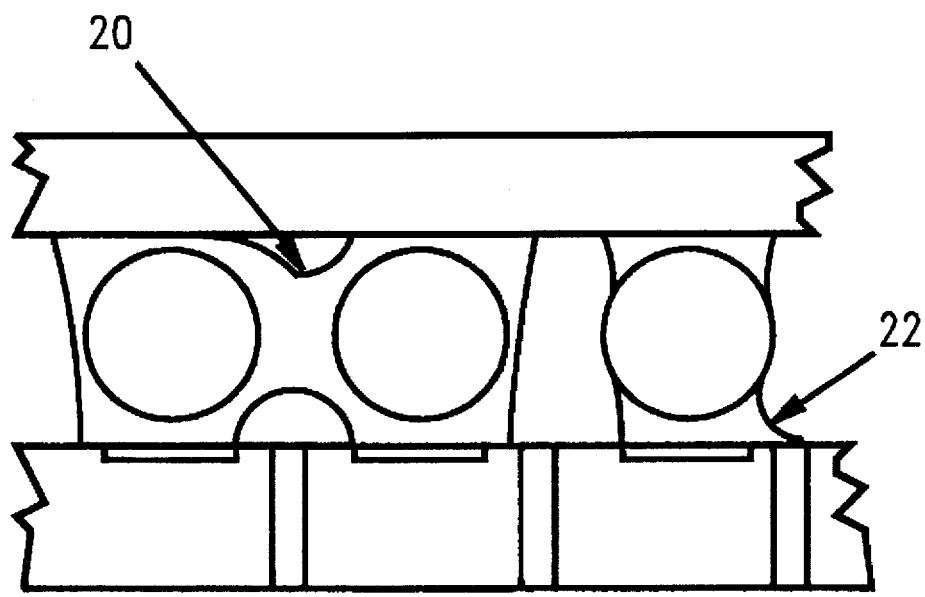
FIG. 4 shows a solder bridging.
Figure 4B:
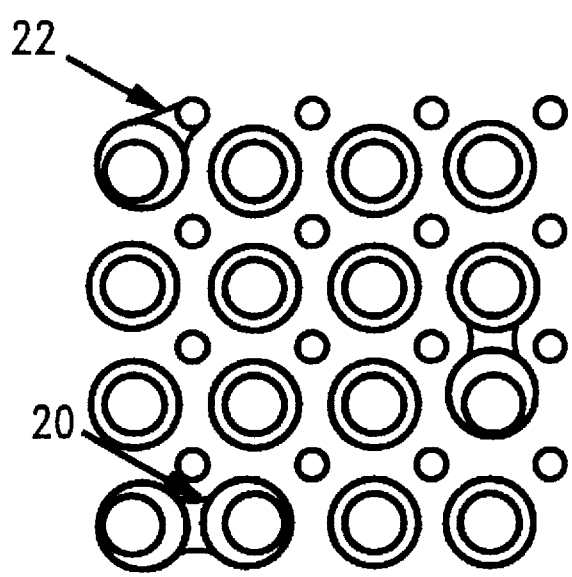

FIG. 4 depicts solder bridging. A solder bridge includes any unwanted solder joining a number of Ball-Grid-Array joints 20 or a Ball-Grid-Array joint to an adjacent via 22. Bridging is due to either: excessive solder paste deposited on the pad, solder-paste misregistration that allows solder paste on adjacent pads to coalesce, excessive placement pressure that causes the solder paste to smear towards an adjacent pad, or contamination on the ball and/or pad that, under the right conditions, causes the ball to misalign during reflow and form a minor bridge with an adjacent ball.

Figure 5:
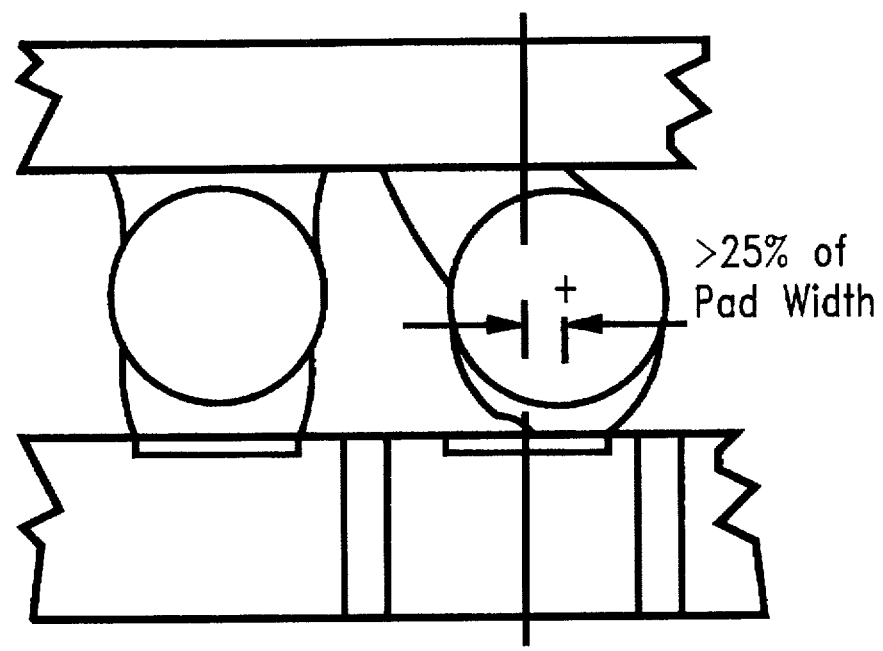
FIG. 5 shows a ball/pad misalignment.
Figure 5:
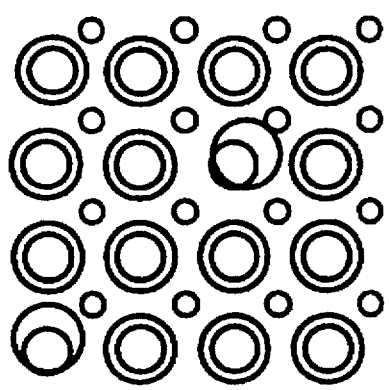
Figure 5:
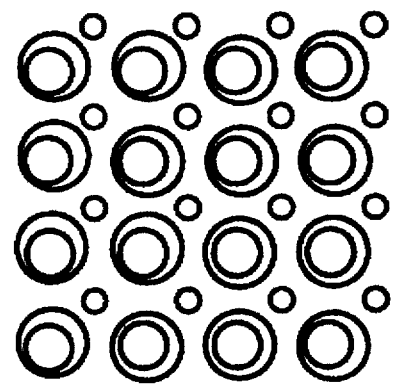

FIG. 5 depicts a ball/pad misalignment. A ball/pad misalignment exists when the horizontal distance between the ball vertical axis and the pad center is greater than 25% of the pad width as shown in FIG. 5a. A misaligned ball can be caused by poor registration of the module combined with insufficient dwell-time during reflow for surface tension to realign the balls, contamination or oxides on the pad and/or ball, or a solder bridge. Whereas contamination is often localized and affects only a few balls (FIG. 5b), poor registration of the module usually causes all the balls (FIG. 5c) on the module to be shifted off center to some extent.

CROSS-SECTIOBAL X-RAY IMAGING

Figures 6A, 6B:
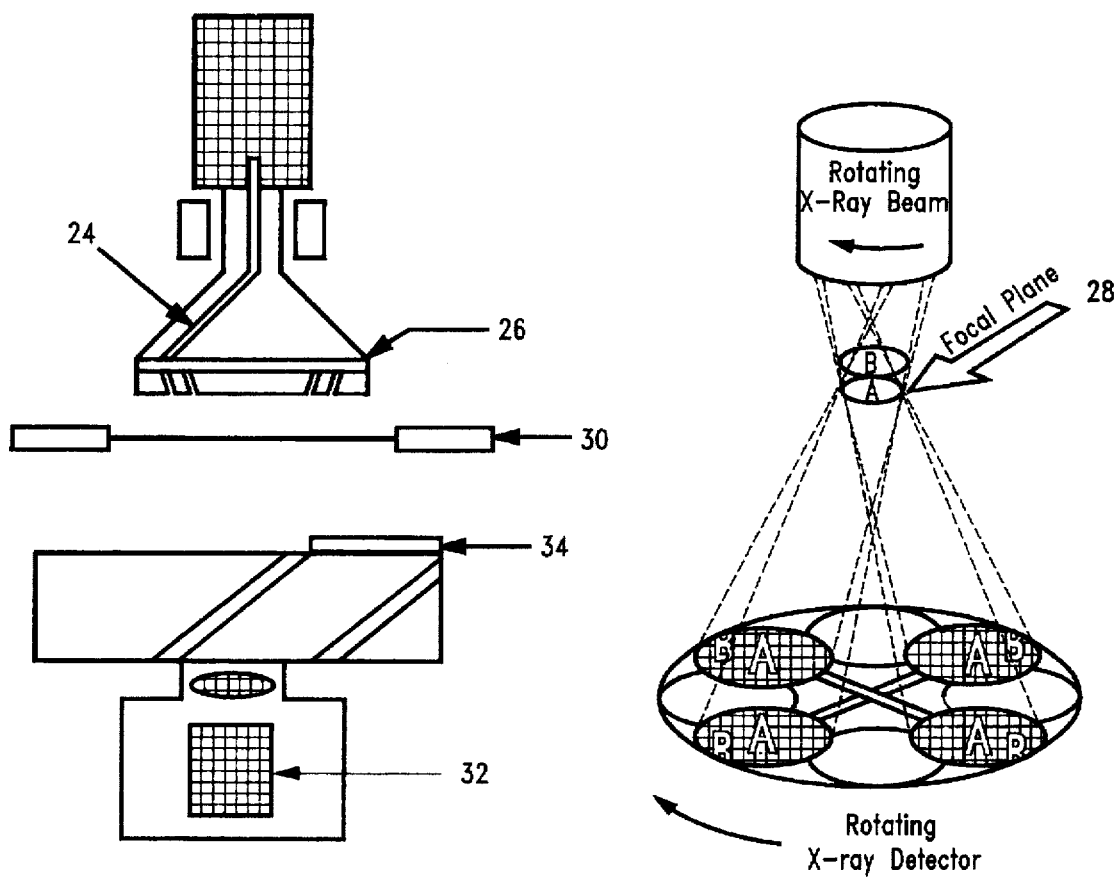
FIG. 6 shows cross-sectional image generation in an X-ray inspection system.

In order to inspect the eutectic-solder fillets of Ball-Grid-Array joints using an X-ray system, the system must be able to focus on a particular cross-sectional plane and, therefore, isolate the solder fillets from the solder balls. Scanned-Beam X-ray Laminography (SBXLAM) is an established automated X-ray technique capable of focusing on a plane of interest to examine features within this plane with great detail and contrast, while defocusing planes above and below to blur features outside the plane-of-interest. The continuous, synchronized motion of the X-ray source and the X-ray detector on separate planes about an axis normal to the plane-of-interest as shown in FIG. 6($b$), mechanically achieves the laminographic effect. By averaging several X-ray images taken during the laminographic motion, a sharp image of the features within the focal plane is produced superimposed on blurred images of vertically-adjacent planes.

The SBXLAM system of FIG. 6 shows an automated inspection system for solder joint inspection. As the electron beam 24 strikes the tungsten target-anode 26 in SBXLAM, it is electrically scanned or rotated about a fixed axis at 600 RPM synchronously with a rotary detector 34 180° out of phase, producing a focal plane 28 at a fixed position. Changing the electron beam scan radius shifts the vertical position of the focal plane which, in turn, changes the magnification factor. The system advantageously has two scan radii resulting in magnification factors ranging from 9.5 to 19 times within Field-Of-Views (FOVs) of respectively 10.2×9.5 mm and 5.1×4.8 mm, and laminographic angles of respectively 28° and 26°. Shifting a printed circuit board (PCB) assembly through the focal plane using a positioning table 30 allows different layers of the assembly to be imaged. A laser range-finder can be used to determine the relative position of the PCB top surface to the focal plane. This system is useful in automated inspection facilities.

In this system, a Silicon-Intensifier-Tube camera 32 captures the image formed on the phosphor screen 34 every 33 ms, and a frame buffer digitizes it, resulting in three images per revolution. Each digitized image consists of 512×480 pixels with 256 gray levels. The image resolution, depending on the size of the FOV, is either 20 µm or 10 µm per pixel. However, the X-ray source focal-spot size, which determines the attainable resolution, is fixed at approximately 16 µm. Several of these images or frames must be averaged in the frame grabber over one or more complete revolutions of the rotary detector to form the final image to be analyzed. Software routines running on one or more computers then analyze the image to measure and classify the joint images.

The SBXLAM system can be calibrated to accurately measure the thickness of solder positioned within the focal plane. The total gray-scale intensity of a solder joint within the focal plane is an additive combination of: a background gray-level due to the blurring of features outside the focal plane, and a delta gray-level due to the solder in the focal plane. To determine the delta gray-level for an area of a solder joint due solely to solder within the focal plane, the average background gray-level of the region surrounding the solder joint is subtracted from the average gray-level of the area in the joint. However, the delta gray-level for a particular solder thickness depends not only on the solder itself but on the background gray-level as well. As the attenuation of the X-ray beam by features outside the focal plane increases, the contrast between a specific solder thickness and its background decreases, which is marked by an increase in the background gray-level and a decrease in the delta gray-level. Therefore, the total calibration between gray-scale intensity and solder thickness for the system involves two steps: the background and delta gray-levels for a range of known solder thicknesses are measured at a typical background gray-level, and the background and delta gray-levels for a constant, known solder thickness are measured at different background gray-levels.

Another technique for generating cross-sectional X-ray images is called digital tomosynthesis, which computationally combines multiple X-ray images taken from different viewpoints to produce a cross-sectional image rather than relying on the mechanical rotation of the detector. Digital tomosynthesis utilizes either a single, large-diameter image intensifier or several small-diameter image intensifiers that remain stationary while a steerable-beam, microfocus tube generates an X-ray beam from N different positions, usually 8 or more, along a horizontal path perpendicular to the vertical axis. The N discrete, projection images are separately stored and computationally combined using various techniques, such as averaging, taking the root to the Nth power, or using a minimum operator, all of which can be applied in an iterative manner to further reduce the image artifacts. A further benefit of digital tomosynthesis is that by shifting the discrete images specific amounts with respect to each other prior to combination brings different planes into focus, and thus, vertical positioning of the object of interest is eliminated. Of course, such a system will require significant computational power to apply the better combination techniques, particularly any iterative ones. While digital tomosynthesis has been developed over the last twenty years for medical applications such as digital angiography, it has only recently been considered as an industrial nondestructive evaluation technique.

The invention herein provides significant improvement in the use of both inspection systems described above, for the purpose of inspecting solder joints.

SUMMARY OF THE INVENTION

The present invention is directed to a method of inspecting an interconnection between components.

In one aspect of this invention, the components to be inspected can include electronic devices or modules such as IC chips or packages, for instance, and substrates on which they are mounted, such as ceramic substrates or printed circuit boards, the interconnections being referred to are the solder joints connecting electrical terminals of the devices with corresponding electrical contacts on the substrates.

A cross-sectional image of an interconnection is generated across the interconnection between components.

A first characteristic of the interconnection is determined by the centroid of the interconnection in the cross-sectional image.

A second characteristic of the interconnection is a measurement with reference to the location of the centroid. This measurement is then compared with a predetermined specification for the purpose of determining the quality of the interconnection. The second characteristic includes a selected region of the perimeter of the interconnection in the cross-sectional image. Alternatively, it can also include a selected region of solder of the interconnection in the cross-sectional image. Finally, it could also include the density of a selected region of solder of the interconnection in the cross-sectional image.

A joint may include different compositions of solder. The first characteristic selected is the centroid of all solders or one composition of solder in the joint; and the second characteristic, the centroid of one of the other solder compositions.

The first characteristic could alternatively include the centroid of one solder composition, and the second, the centroid of a second solder composition.

Another aspect of the invention provides a method of inspecting an interconnection in which cross-sectional images of the interconnection across different positions are generated along the longitudinal axis of the interconnection between the components.

The centroid of the interconnection in one of the cross-sectional images can be chosen to be the first characteristic.

A second characteristic of the interconnection is a measurement with reference to the location of this centroid. This measurement is compared with a predetermined specification for the purpose of determining the quality of the interconnection.

In a third aspect of the invention, the second characteristic can be a selected region or perimeter of the interconnection in any cross-sectional image.

The second characteristic can also be the centroid of a selected region of solder of the interconnection in any cross-sectional image. It can also be the density of a selected region of solder of the interconnection in any cross-sectional image.

A fourth aspect of the invention provides a method of inspecting solder joints between components wherein a cross-sectional image of the interconnections is generated across the interconnections extending between the components and the location of a first characteristic (the centroid) and is determined for each interconnection in the cross-sectional image.

A second characteristic of each interconnection is then measured with reference to the location of the centroids.

The relationship between the measurements of the second characteristics and the location of the centroids is compared to a predetermined specification for the purpose of determining the quality of the interconnections.

The invention herein applies to X-ray inspection systems and can be implemented in software. It can also be used to analyze images produced by off-line inspection systems using data processing devices, such as computers.

DETAILED DESCRIPTION OF THE INVENTION

Preferred embodiments of this invention were developed to optimize the inspection of joints. Due to the type of defects expected, particular implementations of the invention were developed to determine the quality of Ball-Grid Array (BGA) joints using scanned-beam X-ray laminography (SBXLAM) to view internal planar structures. Ball-Grid-Array joint features were measured including the ball/pad alignment, the solder thickness, and the average joint-diameter. These measurements were used to identify defective Ball-Grid-Array joints.

1.1 Measurement of Ball-Grid-Array Features

From the examination of the laminographic X-ray images of nominal and defective Ball-Grid-Array joints, the features that were found to characterize Ball-Grid-Array joints and the image-slices in which to measure them are:

(1) Ball/Pad offset (measured at both Ball and Pad Slices);
(2) the average solder-thickness at the perimeter; and
(3) the average joint-diameter (measured at both Pad and Package Slices).

Furthermore, measurements were taken in the region surrounding the Ball-Grid-Array joints to check for bridges. Additional measurements, particularly solder-thickness measurements, can also be taken to further characterize the Ball-Grid-Array joints and improve the accuracy of the classification process. From an analysis of these features of the laminographic X-ray images that characterize the nominal Ball-Grid-Array joints and identify the defective Ball-Grid-Array joints, the method of the present invention was developed to perform the necessary measurements and classify the Ball-Grid-Array joints to ascertain their acceptability.

A number of Ball-Grid-Array joint features may be required to identify more than one process defect, as well as to characterize Ball-Grid-Array joints for process control. Rather than each inspection routine repeating measurements previously taken, the first routine to analyze the current field of view takes the necessary measurements to characterize the Ball-Grid-Array joints and makes them available to subsequent defect-identification routines. Therefore, with the exception of the routine that detects solder bridges, defect-identification routines do not take measurements to identify their respective defects.

Figure 7:
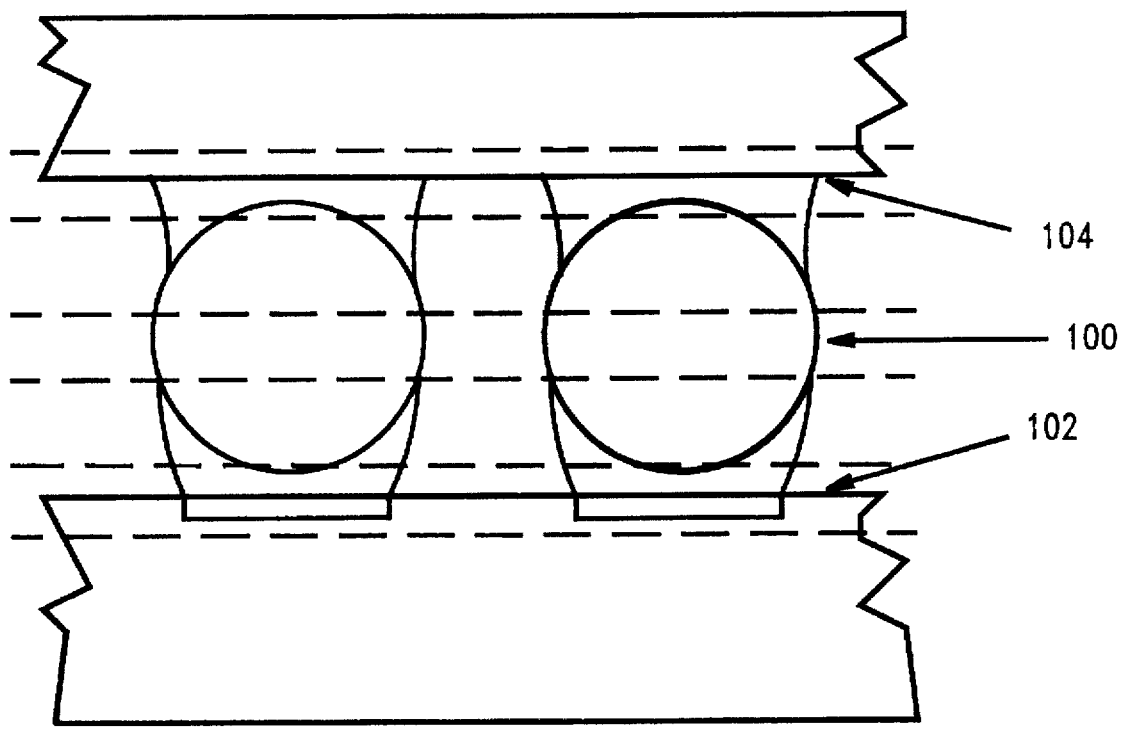
FIG. 7 illustrates typical positions for taking cross-sectional images (image slices).

The first routine, (the measurement routine), referred to as MEASURE, takes common measurements for each joint at three specific image-slices, preferably in the order shown in FIG. 7: Ball Slice 100, Pad Slice 102, and Package Slice 104. Before taking measurements at the Pad Slice and at the Package Slice, MEASURE first locates the centroids of the solder balls in the X-Y plane at the Ball Slice. Determining the ball centroids at the Ball Slice ensures that the solder balls are located accurately without interfering with either the Pad fillet or the Package fillet. Once MEASURE finds the ball centroids, the pad centroids can be located in a similar manner, using the design data for the card being inspected that locates the pad centroids within the Pad Slice. Since most cards are designed with Computer Aided Design (CAD), CAD data is used as a first estimate of the centroid location which is subsequently refined by the techniques described herein. It is important to locate the ball centroid first because the position of the solder ball with respect to the pad determines the shape of the Pad and the Package fillets. At the Pad and Package Slices, MEASURE performs three basic tasks on each joint: it measures the local background gray-level, the average solder-thickness in three annular rings positioned with respect to the ball and pad centroids, and determines an average joint-diameter by using both the solder-mass contour and solder-edge measurements.

(a) Location of Solder-Ball Centroid in the X-Y Plane (Ball Slice).

Since the solder ball can move in any direction, in order to minimize the surface free-energy of the Pad and Package fillets, its centroid must be located to properly adjust the positions of the regions of interest (ROIs) for all subsequent measurements. Three basic image-processing routines: a weighted centroid routine, a spoke edge-detector routine, and a "donut"-operator routine, are used sequentially in the following procedure to locate the ball centroid within the Ball Slice, as shown in FIG. 8.

(i) A circular Region of Interest (ROI) 36 is centered at the pad centroid defined by the design data for the card (FIG. 8a). Its radius is equal to the pad radius plus half the distance between adjacent pads, termed the Inner Pad Distance (IPD). In the embodiment described herein, only the darkest pixels within the ROI are used to determine a weighted-centroid of the image studied as the first estimate of the ball centroid.

(ii) Referring to FIG. 8(b), from the weighted-centroid 38 position, eight spokes 38 are extended to the edge of a circular region of interest with a diameter at least 20% greater than the nominal ball-diameter. The gradient of gray level values of the image is calculated along each spoke, and the ball edge is located at the point of the maximum absolute gradient. The eight edge-points are then used for the second estimate of the ball centroid and its radius by applying the technique developed by Thomas and Chan in the article "A Simple Approach for the Estimation of Circular Arc Center and Its Radius", published in Computer Vision, Graphics, and Image Processing, No. 45, pp. 362–370, 1989.

(iii) Referring to FIG. 8(c), a rectangular donut operator 40, consisting of an outer 42 and inner region 44, is used to locate the position of the maximum average solder-thickness as the final estimate of the ball centroid. As the donut operator is centered sequentially on each pixel along a defined straight path, the difference between the average gray-levels in the outer and the inner region of the operator is calculated for each pixel. The pixel with the maximum negative difference is the position of the maximum average solder-thickness. To make the final estimate of the ball centroid, the donut operator is first run in the X direction, centered at the second estimate of the ball centroid and then, in the Y direction, centered at the adjusted X from the first pass and the Y of the second estimate of the ball centroid. The pixel identified in the final pass of the donut operator is used as the position of the ball centroid, referred to as the first characteristic.

Referring to FIG. 8(d), the actual pad centroids are then determined in a manner similar to the Pad Slice. MEASURE subsequently calculates the distance between the ball centroid 46 projected to the plane of the pad (its X-Y position) and the pad centroid 48, i.e., the ball/pad offset 50. The solder ball X-Y position 46 and the total ball/pad offset 50 are then stored in the global data-area.

(b) Measurement of Local Background Gray-level (Pad and Package Slices)

The measurement routine determines a local background gray-level for each solder fillet, which is necessary for subsequent solder-thickness measurements. From a frequency histogram of pixel gray-levels generated inside a circular ROI that circumscribes both the pad and the fillet, the weighted average gray-level is calculated for the "background" (pixels with the lowest gray-levels). This value is stored as the local background gray-level in the global data-area. The pixels with the highest gray-levels represent the solder in the pad region. The weighted average of these pixels is used to calculate the average solder-thickness for the pad region.

(c) Measurement of Ring-Structure Characteristics (Pad and Package Slices)

Figure 9:
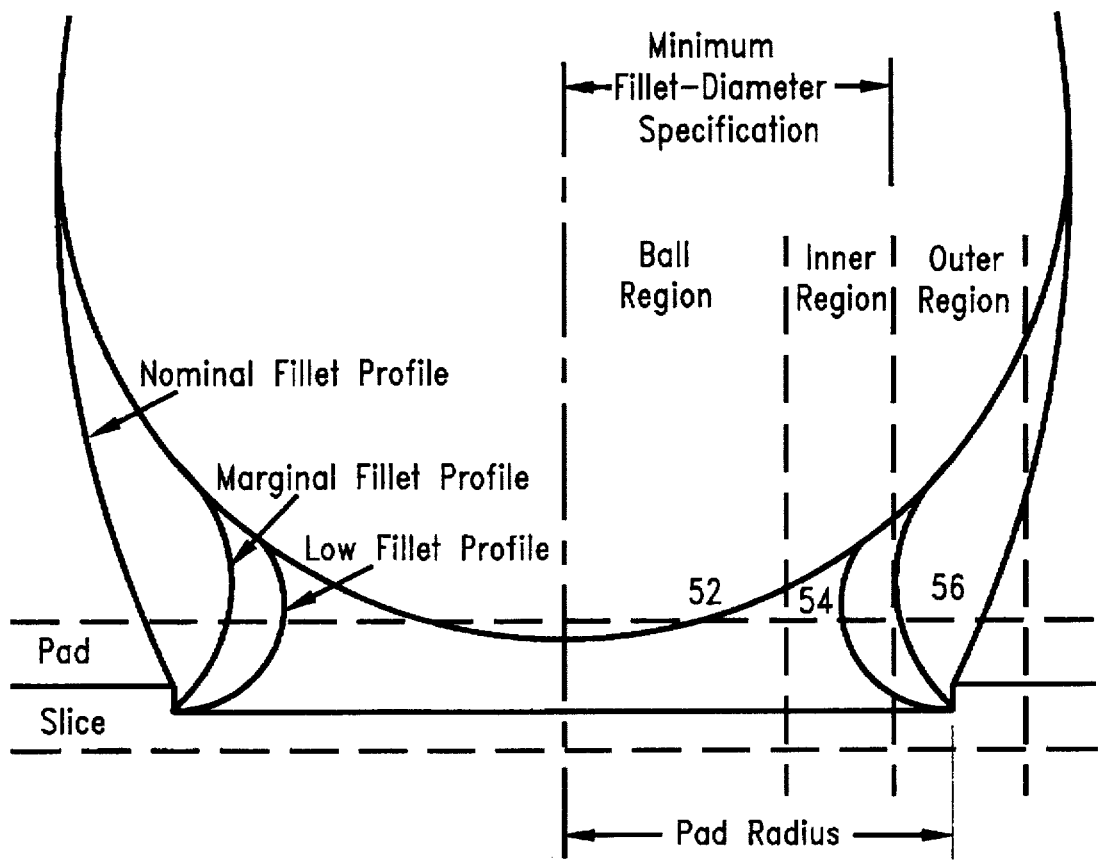
FIG. 9 shows a solder distribution in a Ball-Grid-Array joint.

The solder distribution in an Ball-Grid-Array joint shown in FIG. 9 is characterized by three ring regions: the central ball region 52, the inner ring-region 54, and the outer ring-region 56. The solder thickness in the central ball region 56 is a good indicator of the proximity of the ball to the focal plane and can be used to normalize the other solder-thickness measurements to account for it. However, the variation in solder thickness between low and nominal solder-joints is most evident in the outer ring-region 56.

Figure 10:
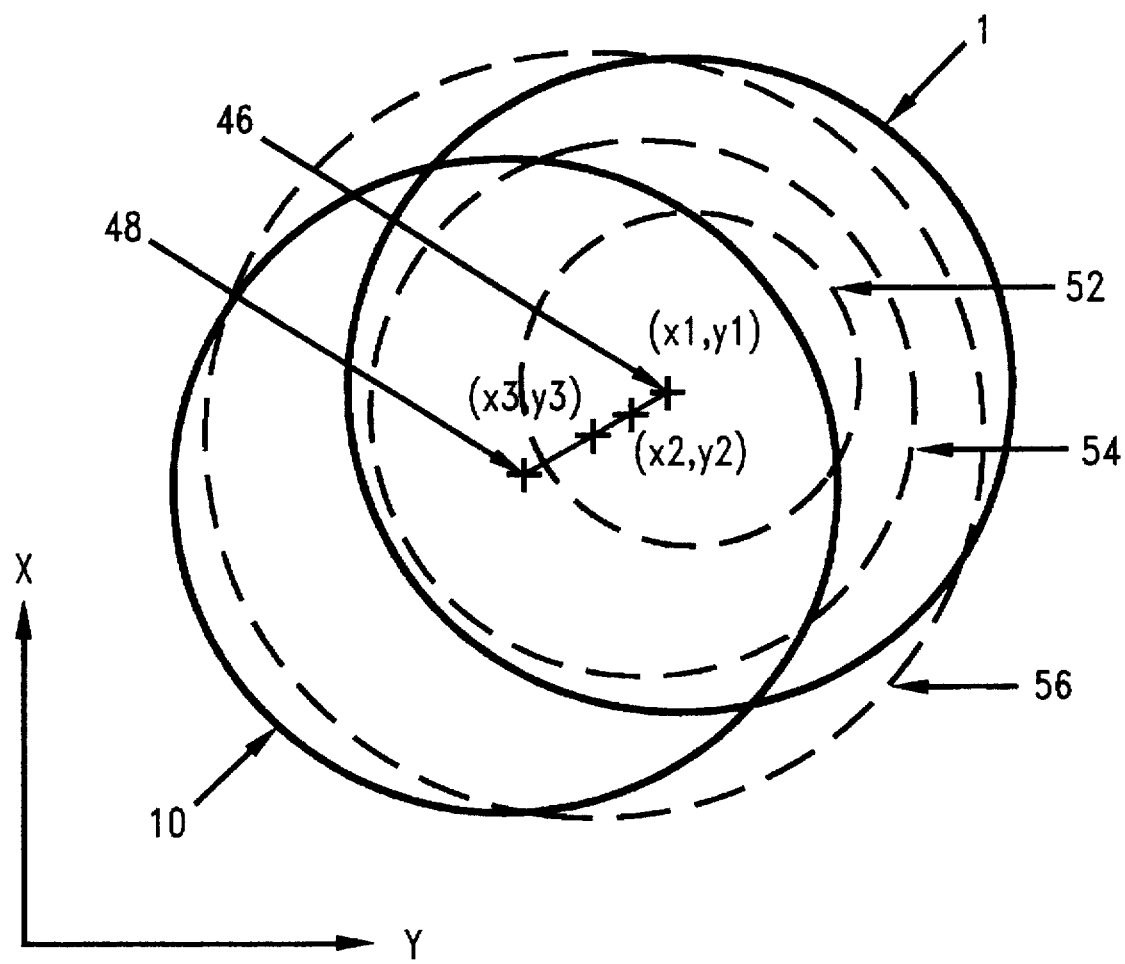
FIG. 10 illustrates a measurement of solder thickness in annular regions positioned relative to joint image centroids.

FIG. 9 represents the ideal case when the ball is aligned with the pad. However, if the ball is offset from the pad, the solder fillet will skew towards the ball, though the annular ring-structure will still be evident. Therefore, the average solder-thickness is measured in three circumjacent rings centered with respect to the offset between the ball centroid and the pad centroid, as shown in FIG. 10. These measurements are taken using the following procedure:

(i) The average solder-thickness is measured in the ball region 52 of the Ball-Grid-Array joint within a circular ROI having a radius approximately 55% of the pad radius.

(ii) The average solder-thickness is then measured between the ball region and the pad perimeter within an inner-ring ROI 54 and an outer-ring ROI 56. Unless the ball 1 and pad 10 centroids coincide, the centers of the circles which define the limits of each annular measurement region do not coincide. Instead, as their radii increase, the circles are progressively centered towards the pad centroid along the line segment between the ball and pad centroids to account for the fillet skew caused by an offset of the solder ball from the pad centroid, as shown in FIG. 10. The radii of Inner Ring 54 and the Outer Ring 56 are, respectively, 85% and 115% of the pad radius.

(d) Determination of Solder-Fillet Extent (Pad and Package Slices)

Figure 11:
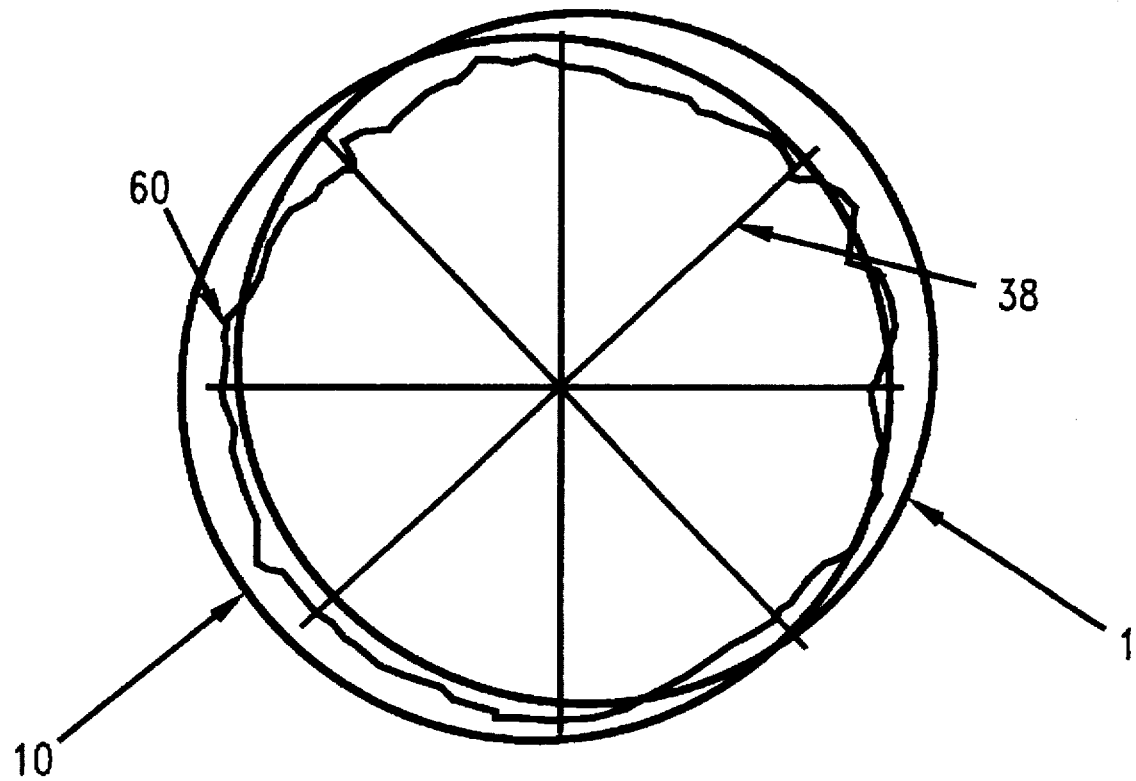
FIG. 11 shows measurement of solder fillet contour and extent.

To characterize the extent of the solder an the pad, the following solder-fillet measurements are taken:

(i) The first measurement shown in FIG. 11 traces a contour 60 around the perimeter of the solder joint connecting all pixels with the same gray-level within a defined circular region of interest. The contour level specifies the total gray-level, (i.e., the additive total of both the background and delta gray-levels), that corresponds to the approximate solder-thickness at the edge of the minimum cross-section of the fillet. The physical cross-sections of nominal and defective Ball-Grid-Array joints revealed that the solder thickness at the edge of the minimum fillet cross-section is typically between 0.05–0.08 mm, about 50–60% of the average solder thickness. The pixels that lie on the contour are then used to estimate the diameter and center of the solder fillet.

(ii) Contour tracing requires a constant background gray-level around the entire Ball-Grid-Array joint, which is not always the case. Therefore, an additional measurement is taken using spoke 38 edge-detection to locate the edge of the solder fillet. From the midpoint of the line segment between the pad centroid and the ball centroid, eight spokes are extended towards the edge of a circular ROI that circumscribes the ball and the pad (FIG. 11). The solder-fillet edge is located along each of the eight spokes using a defined edge threshold. As with the contour pixels, the eight edge-pixels are used to determine the average diameter or extent of the solder fillet. Unlike (i), this measurement Is not dependent on the solder-thickness calibration.

1.2 Open/Low-Solder Identification Routine

The routine for identifying an open or low-solder condition uses the following measurement and ratio to determine whether an open/low-solder condition exists at an Ball-Grid-Array joint:

(i) Average solder-thickness on the pad, Section 1.1.(b).

(ii) Average solder thickness in the ball region, and in the inner and outer rings around the ball region, Section 1.1.(c).

(iii) Average diameters of the solder-fillet contour, Sections 1.1.(d).

(iv) Ratio of the outer-ring thickness multiplied by the inner-ring thickness and divided by the ball-region thickness, herein referred to as the Outer-Inner-Ball (OIB) ratio. This normalization ratio is used because the above measurements are all sensitive to the proximity of the solder ball to the focal plane. Dividing by the ball-region thickness compensates for this effect, while multiplying by the inner-ring thickness strengthens the signal of a open/low-solder condition.

Depending on the results of the comparison of these measurements and the OIB ratio to their thresholds, the open/low-solder routing determines whether the Ball-Grid-Array joint has an open/low-solder condition.

1.3. Pad-Nonwet Identification Routine

If an open/low-solder condition exists at the Pad Slice for an Ball-Grid-Array joint, the pad-nonwet routine uses the same measurement and OIB ratio as the open/low-solder routine, though taken at the Package Slice, to identify an excess-solder condition. If any of the measurements or the OIB ratio is greater than its threshold, the routine classifies the joint as having a pad-nonwet condition.

1.4 Ball/Pad Misalignment Identification Routine

The routine for identifying a ball/pad misalignment compares the distance between the ball centroid and the pad centroid to the user-defined maximum ball/pad offset to determine whether the ball is misaligned. The maximum user-defined threshold is specified as a percentage of the pad width.

1.5 Solder-Bridge Identification Routine

Before attempting to locate a solder bridge on a particular image-slice, the routine first compares the average solder-thickness on that slice to a user-established minimum threshold. If the average solder-thickness is less than the threshold, the routine does not analyze further the joint. Otherwise, it proceeds to take measurements to determine whether a solder bridge is present around the joint, its size, and its angular displacement with respect to the joint.

(a) Check for Major Bridges

Figure 12:
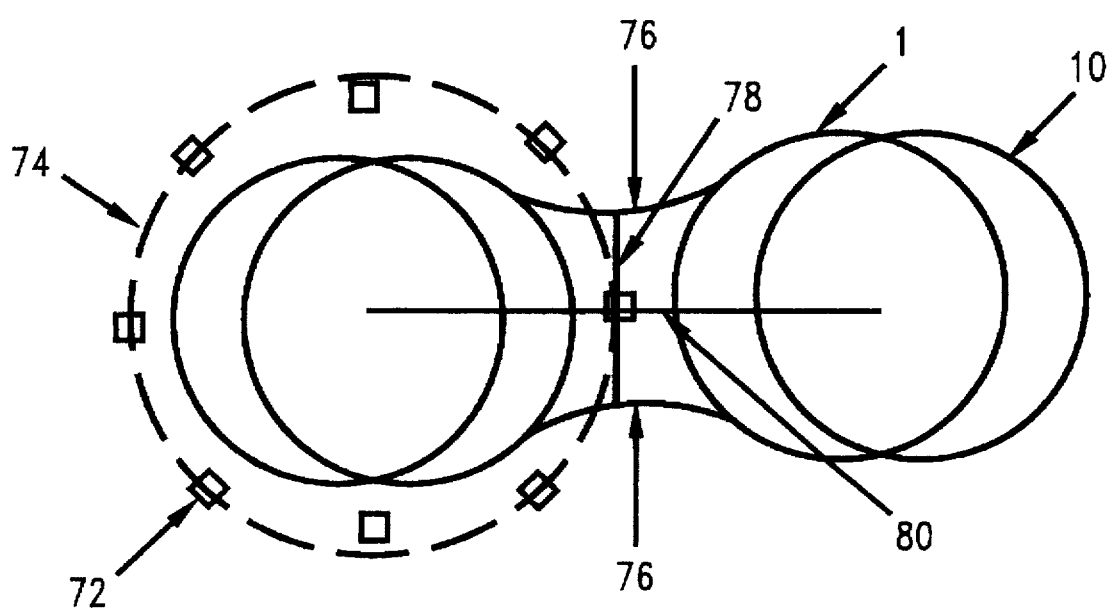
FIG. 12 shows a solder bridge checks.

The major bridges can be found by measuring the delta gray-level above the average background gray-level in small regions outside the joint region along the principal directions towards adjacent Ball-Grid-Array joints. The routine performs the check for major bridges in the following manner:

(i) Referring to FIG. 12, eight square regions 72 are defined around the joint along an ellipse (not outlined) that circumscribes both the ball and the pad, and is positioned relative to the ball and pad centroids. The solder thickness is measured in each region and compared to a user-established threshold.

(ii) If the solder thickness is greater than the threshold, the spoke edge-detection technique, described in Section 1.1.(a), is used to find the longitudinal edges 76 of the bridge and determine a width 78 of the bridge along it.

(iii) A spoke edge-detection technique is also used to find the length of the bridge 80 to ensure that the bridge extends to an adjacent Ball-Grid-Array joints or to an interstitial via. The bridge width and extent are then compared to user-defined thresholds and, if both measurements are greater than the thresholds, a major bridge is identified. If no major bridge is found, the routine proceeds with a check for minor bridges.

(b) Check for a Minor Bridge

Though minor bridges have gray-levels greater than the average background gray-level, they may be missed during the major-bridge check. However, their most definitive features are their distinct edges. Accordingly, the minor bridges can be found by searching for edges along a circular path outside the joint region. The routine performs the check for minor bridges in the following manner:

(i) A circular path 74 shown in FIG. 12 is defined outside the ball/pad area, with its center at the midpoint of the line segment between the ball centroid and the pad centroid and its circumference passing through the midpoint of the line segment between the pad centroid and the centroid of the adjacent pad closest to the ball. Gradient measurements are then taken along the path to locate local gradient-extrema with absolute values greater than a user-established threshold, indicating possible edges of solder bridges. When locating local gradient-extrema, consecutive gradient maxima and minima are paired as the endpoints of a line segment under the assumption that they indicate the leading and trailing edges of solder bridges. Only those local gradient-extrema pairs that meet a minimum height/width ratio are selected.

(ii) For each local gradient-extrema pairs returned by the edge search, the width of the bridge and its angular displacement relative to the pad centroid is determined. As with the major-bridge check, the spoke edge-detection technique is used to find the extent of the bridge to ensure that the bridge extends to an adjacent Ball-Grid-Array-joints or to an interstitial via. The bridge width and extent are compared to user-defined thresholds. If both measurements are greater than the thresholds, a minor bridge is identified; otherwise, if the bridge width is greater than the threshold but does not extend beyond the joints, a further check is performed.

(iii) The contour-tracing technique described in Section 4.1.(d) is used to measure the extent of the solder within a square ROI that extends to the centroids of all eight adjacent Ball-Grid-Array joints. The contour level is set to the average gray-level between the two edges. If the solder contour reaches the perimeter of an adjacent joint or an interstitial via, a minor bridge is identified.

Figure 13A:
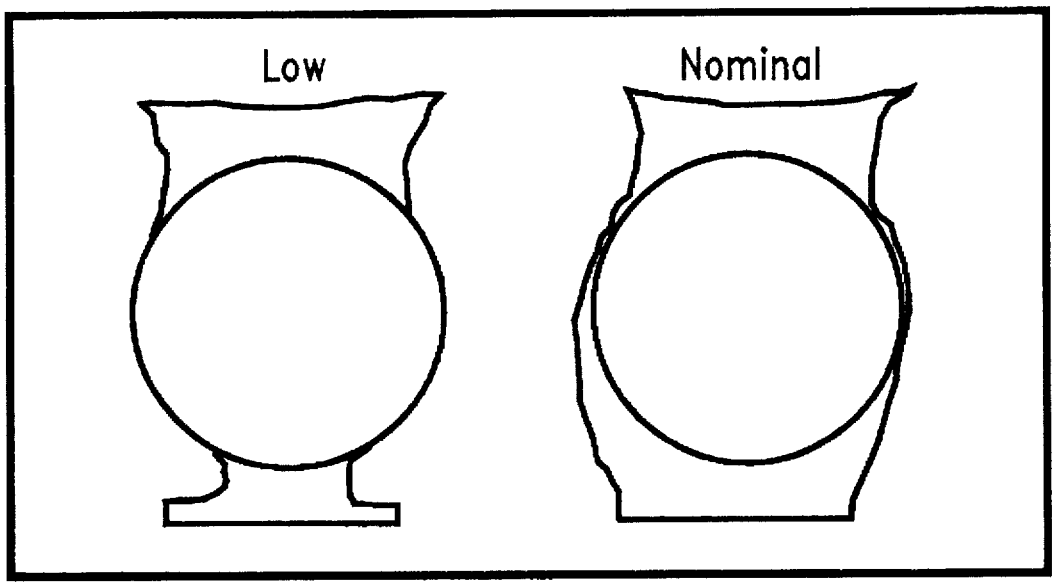
FIG. 13(a) illustrates a low-solder joint and a nominal joint.
Figure 13B:
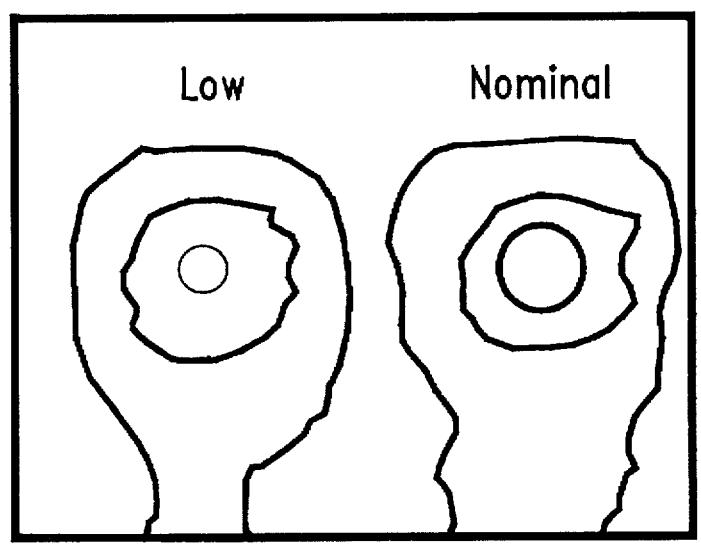
FIG. 13(b) shows the corresponding X-ray image at pad slice.

FIGS. 13(a) and 13(b) illustrate a comparison between physical conditions and X-ray images. The invention herein is adapted to interpret X-ray images to determine joint quality.

Figure 14A:
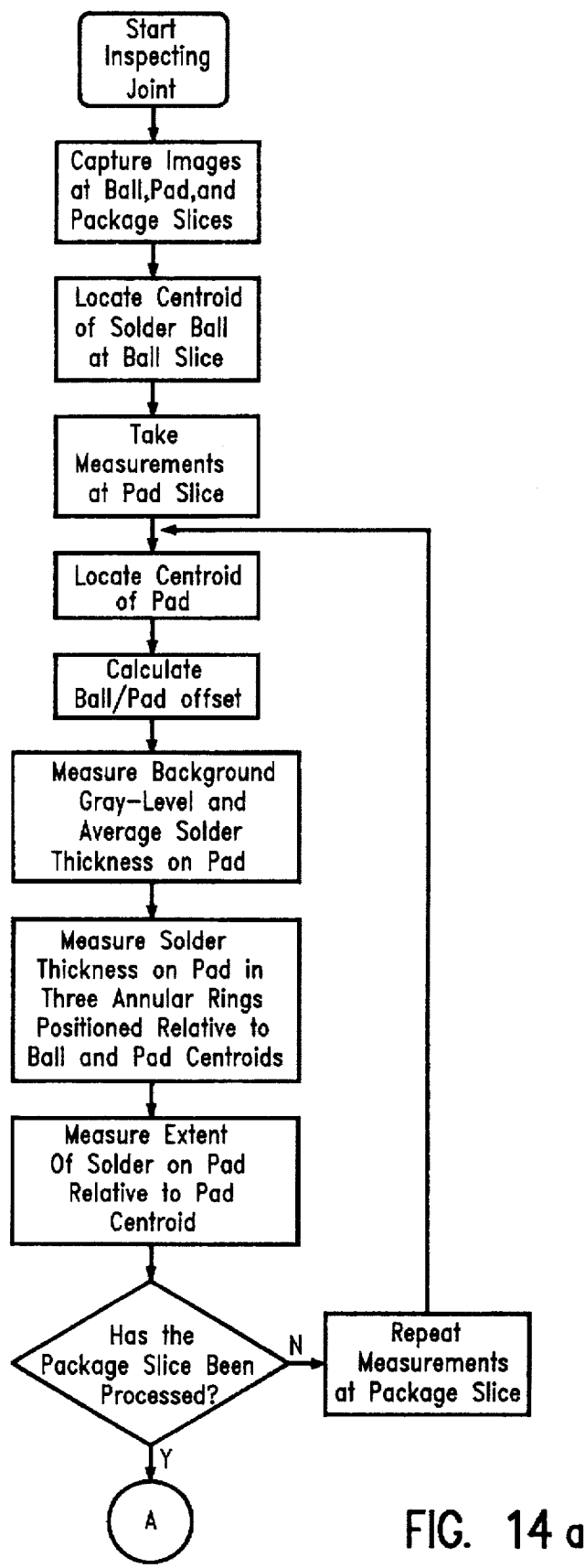
FIG. 14 shows a flow chart of the present invention for the inspection of a solder joint.
Figure 14B:
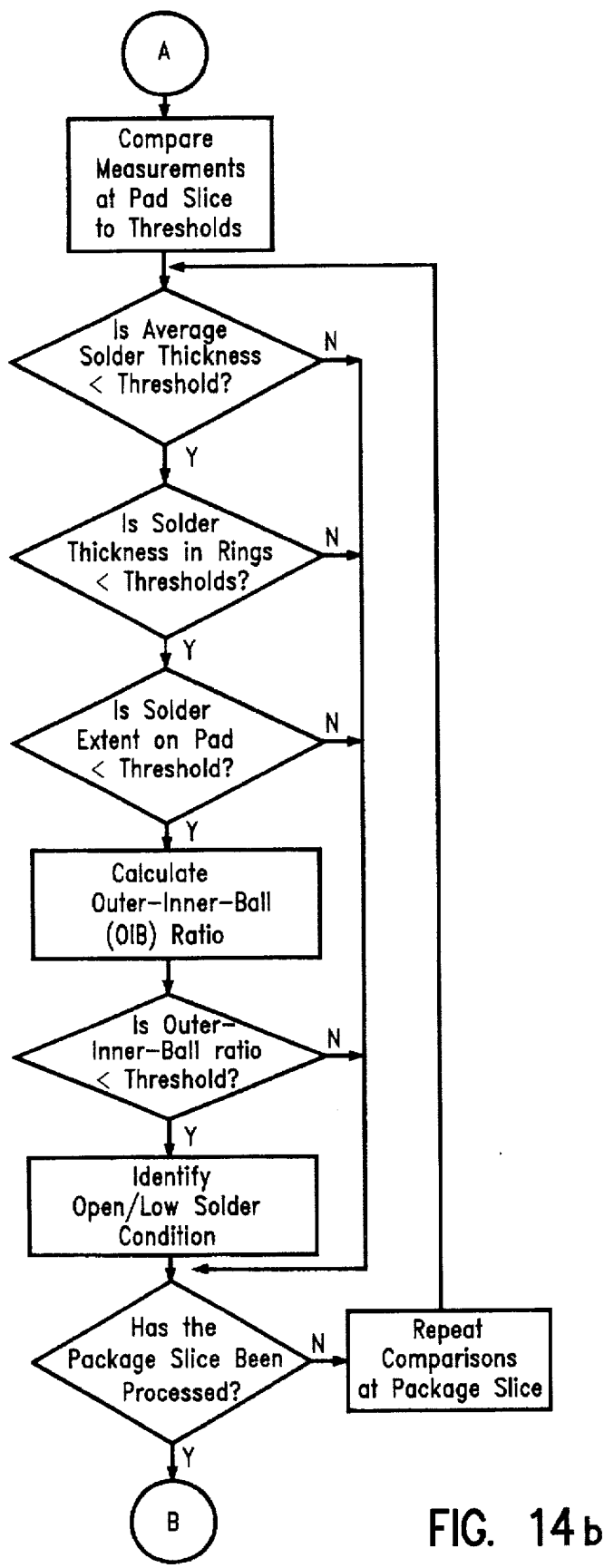
Figure 14C:
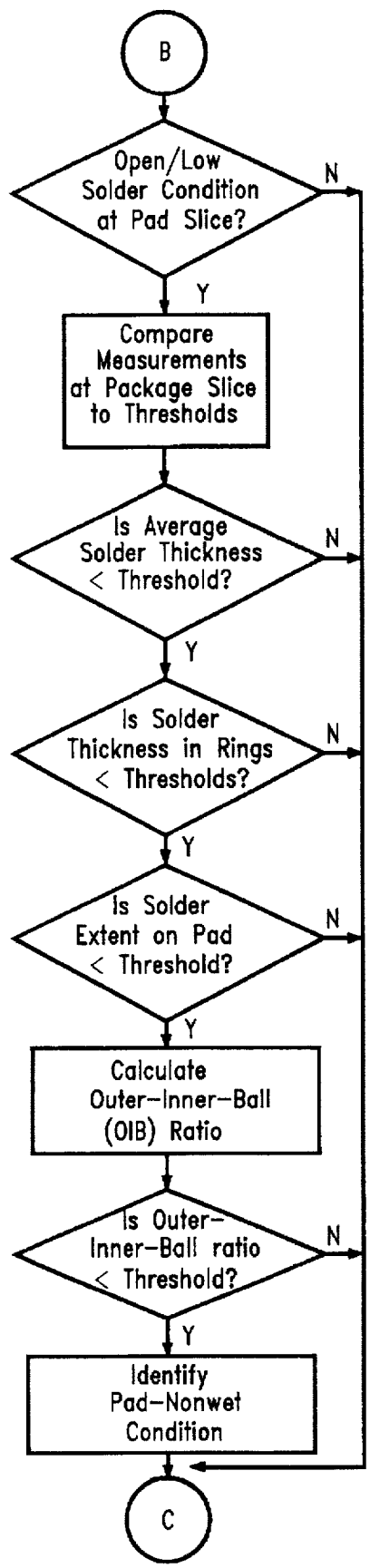
Figure 14D:
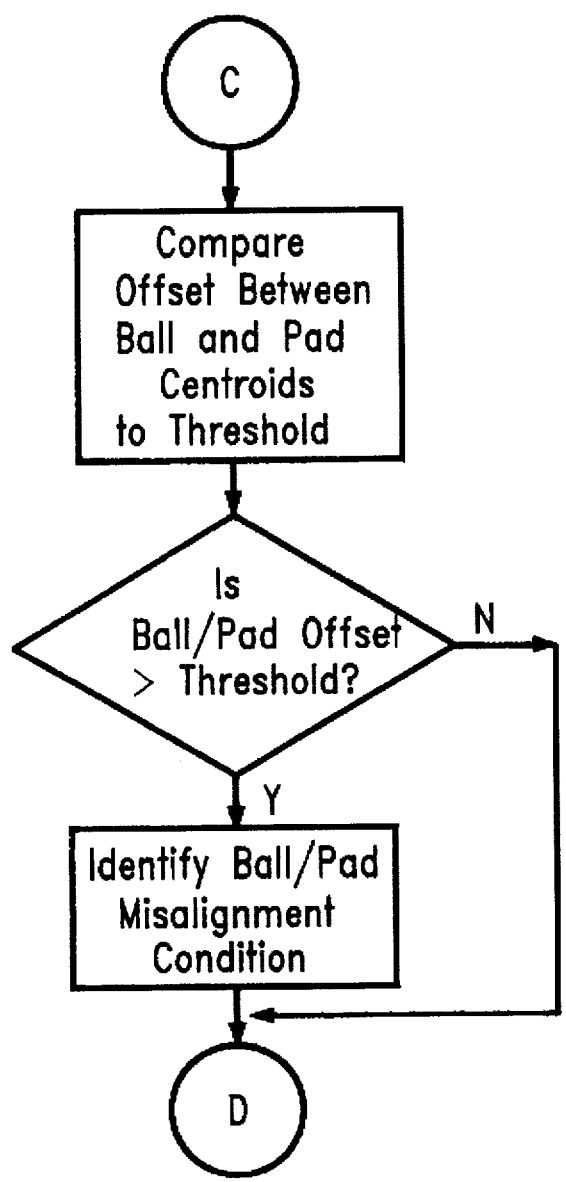
Figure 14E:
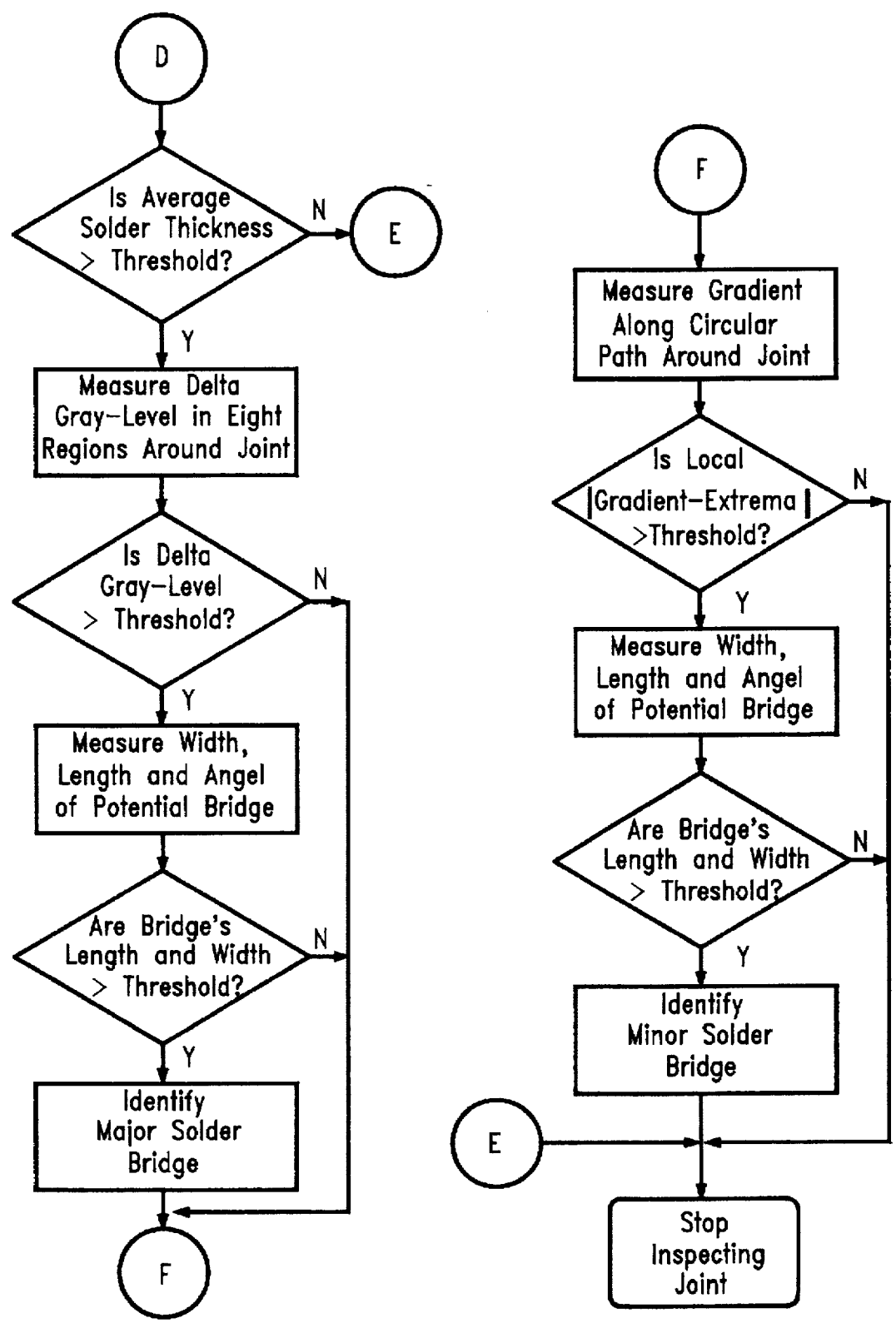

A flow chart of a preferred embodiment of the invention illustrating its use in inspecting a solder joint is presented in FIG. 14, wherein FIG. 14(a) is a measurement routine; FIG. 14(b) illustrates an open-low solder identification routine; FIG. 14(c), a pad non-wet identification routine; FIG. 14(d), a ball-pad misalignment identification routine; and FIG. 14(e), a solder bridge identification and measurement routine.

What is claimed is:

1. A method of inspecting a bonded joint between a first and a second component at connectors of said components, comprising the steps of:

using cross-sectional images of said joint generated:

in a first plane intersecting said joint at:

a) a position substantially medial of said joint between said components, and in a second plane at one of:

b) a position substantially at said first component, and b1) a position substantially at said second component;

determining the location of the centroid of said bonded joint in said cross-sectional image taken at said medial position;

determining the location of the centroid of said bonded joint in one of said cross-sectional images taken at a connector of one of said first and second components;

measuring an offset of said joint by comparing the position of the centroid of said joint taken in said first plane to the position of the centroid of said joint taken in said second plane; and comparing said offset to a predetermined value to determine the acceptability of said joint.

2. The method of inspecting a bonded joint as recited in claim 1, further comprising:

adjusting subsequent measurements of said bonded joint in said cross-sectional image taken in said second plane based on said offset to account for the shape of said bonded joint; and comparing the measurement of said joint at a connector of one of said components with a predetermined value for the purpose of determining the acceptability of said joint.

3. The method of inspecting a bonded joint as recited in claim 1, further comprising the steps of:

measuring the thickness of said bonded joint in said cross-sectional image taken in said second plane, in at least one region that is defined by said centroid of said joint taken at said connector and by said offset of said joint; and comparing said thickness of said joint to a predetermined value to determine the acceptability of said joint.

4. The method of inspecting a bonded joint as recited in claim 1, further comprising the steps of:

measuring geometrical dimensions of said joint in said cross-sectional image taken in said second plane, in at least one region that is defined by said centroid of said joint taken at said connector and by said offset of said joint; and comparing said geometrical dimensions of said joint to a predetermined value to identify whether said joint is defective.

5. The method of claim 1, wherein measuring said joint at said connector of one of said components further comprises measuring a selected region of the perimeter of said joint in said cross-sectional image.

6. The method of claim 1, wherein said measuring said joint at said connector of one of said components further comprises measuring a selected region of bonding material of said joint in said cross-sectional image.

7. The method of claim 1, wherein said measuring said joint at said connector of one of said components further comprises measuring the density of a selected region of bonding material of said joint in said cross-sectional image.

8. The method of inspecting a bonded joint as recited in claim 1, further comprising the steps of:

checking for the presence of bonding material between said bonded joint and adjacent said bonded joints in at least one region that is defined by said centroid of said joint at said connector and by said offset of said joint; and comparing said presence of bonded material in said at least one region to a predetermined specification to determine whether said bonded joint is bridged to adjacent said bonded joints.

9. A method of inspecting a bonded joint between a first and a second component at connectors of said components, comprising the steps of:

using penetrating radiation to generate cross-sectional images of said joint generated:

in a first plane intersecting the longitudinal axis of said joint extending between said components at:

a) a position substantially medial of said joint between said components, and in a second plane at one of:

b) a position substantially at said first component, and b1) a position substantially at said second component;

determining the location of the centroid of said bonded joint in said cross-sectional image taken at said medial position;

determining the location of the centroid of said bonded joint in one of said cross-sectional images taken at a connector of one of said first and second components;

determining an offset of said joint by comparing said image of the centroid of said joint taken at said medial position to said image of the centroid of said joint taken at said connector; and comparing said offset to a predetermined value to determine the acceptability of said joint.

10. The method of inspecting a bonded joint as recited in claim 9 further comprising:

comparing the measurement of said joint at a connector of one of said components with a predetermined specification for the purpose of determining the quality of said joint.

11. A method of inspecting a solder joint between components comprising the steps of:

generating cross-sectional images of the joint in a plurality of substantially parallel spaced planes intersecting said joint, determining the location of a first characteristic of said joint comprising the centroid of said joint in one of said cross-sectional images;

measuring a second characteristic of said joint in reference to the location of said centroid of said joint in another of said other cross-sectional images; and comparing the location of said first and second characteristics of said joints with a predetermined specification for the purpose of determining the quality of said joint.

12. The method of claim 11, wherein said components comprise an electronic module and a substrate to which said module is mounted, said solder joint comprising a soldered connection between a termination of said electronic module and a corresponding connection means on said substrate, and said cross sectional images comprising images across said termination and across said connection means proximate to said joint, and across a central portion of said solder joint.

13. The method of claim 11, wherein measuring said centroid of said joint in another said other cross-sectional images further comprises measuring a selected region of the perimeter of said interconnection in any of said cross-sectional images.

14. The method of claim 11, wherein measuring said centroid of said joint in another of said other cross-sectional images further comprises measuring a selected region of solder of said joint in any of said cross-sectional images.

15. The method of claim 11, wherein measuring said centroid of said joint in another of said other cross-sectional images further comprises measuring the density of a selected region of solder of said joint in any of said cross-sectional images.

16. The method of claim 11, wherein said solder joint comprises multiple compositions of solder, said first characteristic comprises the centroid of all solder in said joint in one of said cross-sectional images, and said second characteristic comprises the centroid of one of said multiple compositions in said solder joint in another said cross-sectional images.

17. A method of inspecting solder joints between components comprising the steps of:

using a stored cross-sectional image of the joints generated in at least one of parallel planes intersecting said joints;

determining the location of a first characteristic of each of said joints, said characteristic comprising the centroid of each said joint in one of said cross-sectional images; and measuring a second characteristic of each of said joints in reference to the location of said centroids, wherein said components comprise a component module having terminations and a substrate to which said electronic component is attached, and said solder joints comprise solder joints for joining said terminations of said electronic component and corresponding substrate connection means on said substrate.

18. The method of claim 17 wherein said components comprise a component module having electrical terminations and a substrate to which said electronic component is attached, said solder joints comprising solder joints for joining said electrical terminations of said electronic component and corresponding electrical substrate connection means on said substrate.

19. The method of claim 17 wherein said cross-sectional images are generated substantially parallel to said component module or substrate; said images being generated at an image plane intersecting said module through said module terminations proximate to said joints, at an image plane intersecting said substrate through said substrate connection means proximate to said joints, and across said joints between said substrate and said module.

20. The method of claim 19 wherein said joints are formed in accordance with ball grid array methods using solder balls for joint formation, wherein said substrate connection means comprises pads for soldering, said cross-sectional image across said substrate is made through said pads, and said cross-sectional image across said joints being made through said solder balls.

21. A method of inspecting multiple solder joints between components comprising the steps of:

using a cross-sectional image of the joints generated in a plane intersecting said joints between said components;

determining the location of a first characteristic of each of said joints, said characteristic comprising the centroid of each said joints in said cross-sectional image; and measuring a second characteristic of each of said joints in reference to the location of said centroids, wherein the relationship between said measurement of said characteristic and the location of said centroids is determined and compared to predetermined specifications for the purpose of determining the quality of said joints.

22. The method of claim 21 wherein measuring said second characteristic comprises measuring a selected region of the perimeter of each said joint in said cross-sectional image.

23. The method of claim 22 wherein the distance between the closest portions of the perimeter of two adjacent joints along a line between the centroids of said two joints is compared to a predetermined specification for the purpose determining the quality of said joints.

24. The method of claim 21 wherein the measurement of said second characteristic of each joint is compared with the central tendency of the measurements of said second characteristics for said joints to determine whether said comparisons satisfy a predetermined specification.

25. A method of inspecting ball grid array solder joints between components comprising the steps of:

generating a cross-sectional image of the joints in a plane intersecting said joints between said components;

determining the location of the centroid of each solder ball in said joints in said cross-sectional image; and measuring a characteristic of each of said joints in reference to the location of said centroids, wherein the relationship between said measurements of said characteristic and the location of said centroids is determined and compared to predetermined specifications for the purpose of determining the quality of said joints.

* * * * *